(12) United States Patent
Stange (10) Patent No.: US 8,236,927 B2
(45) Date of Patent: Aug. 7, 2012

(54) STABILIZER MOLECULE-DEPLETED ALBUMIN SOLUTION

(75) Inventor: Katrin Stange, Rostock (DE)

(73) Assignee: Albutec GmbH, Rostock (DE)

( * ) Notice: Subject to any disclaimer, the term of this patent is extended or adjusted under 35 U.S.C. 154(b) by 1069 days.

(21) Appl. No.: 11/920,015

(22) PCT Filed: May 11, 2006

(86) PCT No.: PCT/EP2006/062234
§ 371 (c)(1),
(2), (4) Date: Jul. 3, 2008

(87) PCT Pub. No.: WO2006/120226
PCT Pub. Date: Nov. 16, 2006

(65) Prior Publication Data
US 2008/0269124 A1    Oct. 30, 2008

(30) Foreign Application Priority Data
May 13, 2005    (DE) .......................... 10 2005 023 155

(51) Int. Cl.
*A61K 38/38*    (2006.01)
(52) U.S. Cl. ............ 530/345; 514/18.8; 435/2; 530/362
(58) Field of Classification Search ........................ None
See application file for complete search history.

(56) References Cited

U.S. PATENT DOCUMENTS

2004/0217055 A1* 11/2004 Kraus et al. .................... 210/645
2004/0228829 A1  11/2004 Roberts et al. ................ 424/78.1
2005/0090652 A1*  4/2005 Bertucci et al. ............... 530/417

FOREIGN PATENT DOCUMENTS

DE         10261910        7/2004
WO         WO 96/37515     11/1996
WO         WO 2004/071524   8/2004

OTHER PUBLICATIONS

Chen, Journal of Biological Chemistry, 1967, vol. 242, No. 2, pp. 173-181.*
Chen, R. F., "Removal of Fatty Acids from Serum Albumin by Charcoal Treatment", The Journal of Biological Chemistry, Jan. 25, 1967, Bd. 242, Nr. 2, 173-181, XP002395537, ISSN: 0021-9258.
Huntley, T. E., et al., "Binding Properties of Purified Adult and Fetal Bovine Serum Albumin", Biochimica Et Biophysica Acta., Bd, 490, Nr. 1, 1977, Seiten 112-119, XP00239538, ISSN: 0006-3002.
Birkett, C., "Serum Protein Delipidation Question", 1995, http://www.bio.net/bionet/mm/proteins/1995-March/002394.html ; ges. Druckschrift.

* cited by examiner

*Primary Examiner* — Christopher R. Tate
*Assistant Examiner* — Roy Teller
(74) *Attorney, Agent, or Firm* — Michael L. Dunn (57) ABSTRACT

The invention concerns a method for producing an aqueous albumin solution from a starting albumin solution which contains stabilizer molecules which are capable of occupying binding sites of the albumin, wherein in a method for increasing the albumin binding capacity (ABiC) for other molecules, at least a portion of the stabilizer molecules is removed from the albumin of the starting albumin solution and separated from the starting albumin solution. To carry out such a method, by means of which a stabilized commercial starting albumin solution can be prepared in a manner which is simpler, faster, cheaper and in a manner which is gently on the albumin by removing the majority of the stabilizers and increasing the albumin binding capacity, the method comprises steps in which the starting albumin solution is brought into contact with a solid adsorption material the affinity of which for at least a portion, preferably all of the stabilizer molecules is higher than the affinity of the albumin for the corresponding stabilizer molecules, and the albumin is separated from the adsorption material; wherein the method is carried out at a pH of >3.

24 Claims, 3 Drawing Sheets

Figure 1

KEY:
Zeitpunkt = Time
vor = before
nach = after
Kontrollgruppe = control group
AbiC optimierte Gruppe = AbiC optimized group

Figure 2

Mean arterial pressure

Figure 3

Systolic blood pressure

Figure 4

KEY:
Zeitpunkt = Time
vor = before
nach = after
Kontrollgruppe = control group
AbiC optimierte Gruppe = AbiC optimized group Diastolic blood pressure

Figure 5

Heart rate

KEY:
Zeitpunkt = Time
vor = before
nach = after
Kontrollgruppe = control group
AbiC optimierte Gruppe = AbiC optimized group

STABILIZER MOLECULE-DEPLETED ALBUMIN SOLUTION

CROSS REFERENCE TO RELATED APPLICATIONS

There are no related Applications

STATEMENT REGARDING FEDERALLY SPONSORED RESEARCH OR DEVELOPMENT

There is no federally sponsored research or development related to this Application

NAMES OF PARTIES TO A JOINT RESEARCH AGREEMENT

This invention is not the subject of a joint research agreement.

REFERENCE TO SEQUENCE LISTING

There are no sequences requiring a sequence listing.

BACKGROUND OF THE INVENTION

The invention relates to a method for producing an aqueous albumin solution from a starting albumin solution, which contains stabilizer molecules, which are capable of occupying binding sites of the albumin, wherein in a method for increasing the albumin binding capacity (ABiC) for other molecules, for example those with physiological effects, at least a portion of the stabilizer molecules is removed from the albumin of the starting albumin solution and separated from the starting albumin solution.

In many severe diseases with resultant organ failure, the mismatch between the capacity of the blood vessels and the volume contained therein plays a central role. If the capacity is too high or the volume is too low, blood pressure drops result and the organs are not sufficiently flushed with blood. If the capacity is too small or the volume too large, blood pressure rises with consequent heart insufficiency and/or lung oedema.

Both sudden and slow volume loss in the blood vessels may be responsible for blood pressure drops with minimum perfusion. Sudden loss in volume may occur when bleeding occurs. Slow volume losses result, for example, from fluid loss by transudation from the vascular bed into the intercellular space due to reducing concentrations of albumin as an oncotic protein (for example when synthesis is affected in liver disease). However, both sudden and slow increases in the capacity of the vessels may also be responsible for blood pressure drops. Sudden vessel expansion results, for example, from an acute cascade of vasodilatory textile hormones, such as histamine, bradykinin, kallikrein, leukotrienes or prostaglandins, which occur during anaphylactic shock. Slow expansions result from a chronic pressure rise in the portal artery linked to an increased presence of vasodilatories in the arterioles of the splanchnic network and result in hepatorenal syndrome with ascites formation via an enlargement of capacity.

In each case there is a mismatch between the capacity and volume, which can be influenced by two treatment strategies.

Firstly, an attempt can be made to increase the intravasal volume by administering crystalloid or colloidal volume replacement solutions. If the mean arterial pressure is not thereby brought into the range which allows sufficient blood flow to all organs, then in the second step "pressors" (vasocontrictors, for example catecholamine) are used which narrow the vessels. Such a vasoconstriction is used particularly when vessel tonus is lost, as occurs in liver disease and sepsis, to try and further reduce the capacity of the vessel system.

In diseases which cause acute or chronic vasodilation through a higher level of vasodilators, maintaining a sufficient blood pressure by infusion for long term volume increase is not possible without vasoconstrictors. Examples of such intensive care medical problems are liver failure with a pressure drop and hepatorenal problems (secondary kidney failure in liver failure due to blood flow problems) or sepsis. Both cases are linked to a high mortality and are expensive medically.

Existing solutions recommend the administration of volume replacement fluids in combination with vasoconstrictors. The time which existing volume replacement fluids spend in the vessels is limited, however. Crystalloid (salt-containing) infusion solutions diffuse quickly into the intercellular space. Volume replacement solutions with polymers, for example starch solutions (hydroxyethyl starch, HAES) or gelatin solutions (Gelafundin) are effective in the vessels for longer, as they have water-binding properties which keep the plasma liquid in the vessel and thus can increase the intravasal volume for a longer period. However, problems arise with artificial polymers due to incompatibility.

A particularly suitable volume replacement means is a solution of the natural colloid serum albumin. Serum albumin has been used in the medical field for decades as a plasma expander and is considered to be the best tolerated biologically and thus the most preferred volume expansion medium, albeit the most expensive.

Solutions of human serum albumin for infusion are commercially available. However, those solutions must be supplemented with stabilizers to allow pasteurization and storage, to avoid the spontaneous polymerization of the albumin. Usually, N-acetyl tryptophan and octanoic acid or their sodium salts are used, alone or in combination. These stabilizers have a very high binding affinity for the albumin molecule and occupy and block important binding sites for the biological function of the albumin.

Meta-analysis has shown that the use of serum albumin solutions in intensive care when compared to other plasma volume replacement solutions was linked to increased mortality (Cochrane meta-analysis in BMJ 1998; 317, p 235-240). With the exception of a few particular indications, then, existing albumin infusion solutions appear to have no clinical advantage. How the production method (fractionation with subsequent pasteurization and stabilization) of existing serum albumin solutions adversely affects the theoretical ideal properties of the serum albumin as a plasma expander, is not currently known. The literature makes inconsistent mention that the stabilizers N-acetyl tryptophan and octanoic acid could under certain circumstances have damaging side effects. Thus, it would be desirable if these stabilizers could be removed before administering the albumin solution to a patient, as these occupy and block binding sites which are required for important functions of the albumin with a high affinity. However, stabilizer-free albumin solutions suffer from the problem mentioned above of spontaneous polymerization of the albumin and thus the poor storage properties of such solutions.

The biologically important ability of human serum albumin to bind ligands is treated in many publications. A comprehensive overview can be found, inter alia, in J. Peters jr., All about Albumin, Academic Press, San Diego, New York, Boston, London, Sydney, Tokyo Toronto, 1996, and in Pacifici G M, Viani A, Methods of Determining Plasma and Textile Binding of Drugs, Clin Pharmacokinet, 1992, 23 (6): 449-468. Because of the enormous variety of methods for determining the albumin binding capacity, the results are difficult to compare and an interpretation as regards its medical relevance is practically impossible.

A novel method for documenting the binding behaviour of albumin is constituted by a measurement of the albumin binding capacity (ABiC) for dansylsarcosin (Klammt S, Brinkmann B, Mitzner S, Munzert E, Loock J, Stange J, Emmrich J, Liebe S, Albumin Binding Capacity (ABiC) is reduced in commercially available Human Serum Albumin preparations with stabilizers, Zeitschrift für Gastroenterologie, Supplement 2001, 39: 24-27). These methods are based on measuring the ultrafiltered part of the test marker dansylsarcosin under predetermined experimental conditions and the relationship of this binding capacity to a reference albumin.

In a comparison between healthy blood donors and patients with serious liver diseases, a significant reduction in the binding capacity of serum albumin was observed which was explained by the greater occupation of the serum albumin binding sites by endogenous ligands as a result of liver detoxification malfunctions in the patients under investigation. It is known that the binding behaviour of commercially available preparations of human serum albumin towards particular model markers (for example Ibuprofen) is also dramatically limited.

It is also known that in a ligand-free albumin, the binding capacity for dansylsarcosin can be reduced from 100% to about 60% if N-acetyl tryptophan is added stepwise in amounts of up to a molar ratio of 1:1 (measured using the ABiC in accordance with Klammt et al, 2001).

The technical and medical literature contains many publications regarding the purification of albumin from donor plasma or from biotechnologically produced (recombinant) albumin. These publications are, however, are primarily concerned with the purest possible preparation of the albumin fraction and the removal of other protein components or potentially toxic components from the blood plasma or, in the case of recombinant production, from the vector system.

The removal of low molecular weight ligands such as stabilizers in commercial serum albumin solutions was carried out up to 1967 using Goodman's methods (Goodman D S, Science, 125, 1996, 1957) based on extraction with a mixture of iso-octane and acetic acid, or William's methods (Williams E J and Foster J F, J Am Chem Soc, 81, 965, 1959), based on spontaneous lipid layer formation in highly acidic media. Both methods are extremely time-consuming and not suitable for the production of therapeutic preparations because of potential toxicity. Albumin solutions produced using those methods have very poor stability on storage.

Since 1967, free fatty acids have been added to albumin solutions as stabilizers, such as octanoic acid, and removed from the albumin solution by rendering it highly acidic and then treatment with activated charcoal. The method was initially published by Chen et al, Journal of Biological Chemistry, volume 212, no 2, 25, January, p 173-181, 1967. In that method, the albumin solution is acidified in distilled water using an acid (HCl) to a pH of 3 or less to unfold the albumin molecule by breaking hydrogen bonds and also to protonate the corresponding fatty acids. This loosens the bond between albumin and the fatty acid to such an extent that the fatty acid can diffuse to the activated charcoal as a small molecule. Next, the albumin solution is mixed with activated charcoal and stirred for 1 hour in an ice bath using a magnetic stirrer. Next, the activated charcoal is separated by centrifuging the mixture at 20200 g. In this method, various fatty acids can be removed. This standard procedure (until now) for the removal of fatty acids is based on detailed investigations of the various conditions such as the pH and the mass ratios of activated charcoal to albumin, wherein the standard procedure described above is by far the most successful. The removal of stabilizers from albumin molecules was thus only achieved by breaking the structure of the albumin molecule and an associated reduction in the binding affinity in a highly acidic medium. Substantial reduction of free fatty acids from human serum albumin at higher pHs of more than 3 was not successful.

An important disadvantage of the method is the structural alteration of the albumin molecule by the considerable acidification in aqueous medium. Herein, not only the loop-forming bonds between amino acids which are separated from each other are cut, but also the hydrophobic binding pockets are opened up, which leads to increased adsorption of the albumin on the activated charcoal which is used. Chen et al note albumin losses of 20% in the charcoal pellet in their method. The method is unsuitable for the primary production of commercial therapeutic albumin solutions as the structural alteration in the albumin molecule triggers a spontaneous polymerization of the human serum albumin on storage.

In a quarter of current medical applications for human serum albumin (HSA) as a volume replacement medium (in total about 200 tonnes per year), in addition to colloid-osmotic properties, intact binding properties for toxins (for example benzodiazepine) play a major role, namely for indications associated with liver disease. This property is, however, limited in commercial preparations by stabilizers (N-acetyl tryptophan and octanoic acid) which occupy binding sites, which is reflected in a reduced albumin binding capacity (ABiC).

BRIEF SUMMARY OF THE INVENTION

Thus, the invention aims to provide a method wherein a stabilized commercial starting albumin solution can be prepared in a simple, fast and inexpensive manner which is gentle on the albumin, for example at the bedside immediately before administration to a patient, removing a major portion of the stabilizers and raising the albumin binding capacity, without damaging the structure of the albumin.

In particular, the method should provide an increase in the albumin binding capacity at the Sudlow II binding site which is of significance for the effectivity in immobilizing endogenous albumin-seeking toxins for all applications of albumin in intravenous volume replacement therapy, but also for extracorporal detoxification procedures, such as plasma exchange against albumin or extracorporal albumindialysis.

This aim is achieved by dint of a method for producing an aqueous albumin solution from a starting albumin solution which contains stabilizer molecules which are capable of occupying binding sites of the albumin, wherein in a method for increasing the albumin binding capacity (ABiC) for other molecules, at least a portion of the stabilizer molecules is removed from the albumin of the starting albumin solution and separated from the starting albumin solution, wherein:

a) the starting albumin solution is brought into contact with a solid adsorption material the affinity of which for at least a portion, preferably all of the stabilizer molecules used, is higher than the affinity of the albumin for the corresponding stabilizer molecules; wherein the method is carried out at a pH of >3; and b) the albumin is separated from the adsorption material.

Particularly preferably, the method is carried out at a pH in the range 5 to 9, more preferably in the range 6 to 8. Particularly preferably, the pH range is 6.9 to 7.5.

The method of the invention allows a commercial, stabilized albumin solution to be prepared close to the administration location without active pH manipulation. The prepared solution contains albumin which has a raised ABiC.

Thus, the properties of human serum albumin as a plasma expander are clinically improved so that the binding power of the albumin is comparable to the physiological transportability of human serum albumin (HSA). Circulatory, kidney and brain functions of patients are positively affected and the cost/benefit ratio is significantly improved.

DETAILED DESCRIPTION OF THE INVENTION

The invention stems from the surprising observation that using a corresponding procedure and using suitable adsorption material, the stabilizers contained in commercial albumin solutions to stabilize and prevent spontaneous polymerization, in particular medium chain fatty acids (for example octanoate), can be removed without a drastic reduction in pH simply, quickly, without any large expenditure and in sufficient amount, and delivers a measurable rise in albumin binding capacity (ABiC). The method of the invention is particularly suitable for the extemporaneous or bedside preparation of commercial stabilized albumin solutions, which can be administered to a patient immediately following preparation. The method has the further advantage that the albumin in the solution is not subjected to extreme conditions such as the drastic drop in the pH used in the prior art to remove the stabilizers from the binding sites of the albumin molecule by breaking bonds between amino acids separated from each other in the albumin chain, which determine loop formation and binding site properties. In the method of the invention, the deleterious structural alteration of the albumin molecule which was known in the prior art does not occur.

Albumin Binding Capacity (ABiC)

The albumin binding capacity (ABiC) in the context of this invention is determined using Klammt et al's method. Firstly, the albumin concentration in an albumin solution is determined by scattering measurements (nephelometry) and the solution is then adjusted to an albumin concentration of 150 µmol/l or 300 µmol/l by dilution. Next, one volume of the albumin solution with a predetermined concentration of a fluorescence marker (dansylsarcosin, Sigma Chemical) which is specific for binding site II (diazepam binding site) of the albumin is added in an equilmolar ratio and incubated for 20 min at 25° C. After incubation, unbound fluorescence marker is separated out by ultrafiltration (Centrisart I, Sartorius Göttingen; exclusion size: 20000 dalton) and the amount of unbound fluorescence marker in the separated solution is determined by fluorescence spectrometry (Fluoroscan, Labsystems, Finland; excitation: 355 nm; emission: 460 nm). To reinforce the fluorescence, the solution of unbound fluorescence marker is supplemented with ligand-free albumin (fatty acid free; from Sigma Aldrich in powder form) in a concentration of 150 µmol/l or 300 µmol/l. Alongside the sample amino acid solution, the same measurement is carried out on a corresponding solution of a reference albumin. The reference is purified and deligandised human serum albumin (BiSeKo, Biotest Pharma GmbH, Dreieich, Germany). Alternatively, the albumin can also be removed from a serum pool of more than 50 healthy blood donors (using Deutsches Rotes Kreuz [German red Cross] criteria). The albumin binding capacity (ABiC) is calculated using the following formula:

$$ABiC[\%] = \frac{conc.\ \text{unbound fluorescence marker(reference albumin)}}{conc.\ \text{unbound fluorescence marker(sample albumin)}} \times 100$$

NB: the albumin binding capacity (ABiC) measured in accordance with Klammt et al and using the above formula does not give the absolute binding capacity of albumin for all of its binding sites, but the relative binding capacity, compared with the reference albumin, for ligands which bind to Sudlow II binding sites (diazepam binding sites). It can thus have a value of more than 100%. The special measurement method is, however, particularly suitable for measuring even the smallest changes in the albumin binding capacity as the marker is particularly easily expelled from the bond.

Normal commercial albumin solutions, which are stabilized with N-acetyl tryptophan and/or octanoic acid or their Na salts, usually have an albumin binding capacity as measured using the determination method described here, of less than 60%. The present invention is based on the use of an adsorption method with an adsorber which at a pH of >3, preferably a pH in the range 5 to 9, has a higher affinity for the stabilizers used (for example octanoic acid and/or N-acetyl tryptophan) than albumin itself. Using the method of the invention, the albumin binding capacity in commercial stabilized albumin solutions can be raised without acidification to more than 100% (with respect to the reference albumin) in less than 30 minutes.

An essential advantage of the method of the invention is that the albumin is not substantially changed structurally under extreme conditions such as severe acidification or the use of denaturing means, but essentially retains its native conformation. Thus, following infusion into a patient, and due to the improved binding capacity following stabilizer removal, a considerably higher activity is obtained than in commercial albumin preparations. A further advantage of the method of the invention is that the stabilized albumin solution can be quickly depleted in stabilizers using cheap and simple apparatus to prepare the stabilizer-depleted albumin solution. Thus, renaturing the albumin after removing the stabilizers, for example by spontaneous regeneration of the inner loop of the albumin, which is linked to the uncertainty of spontaneous formation of depleted or polymerized albumin molecules, is not necessary. Normally, after depletion, the albumin solution of the invention is fed only through a particle filter with a pore size of more than 65000 daltons, to remove any coarse particles which may be present. This allows the method to be carried out close to the point of administration (for example at the bedside).

Since as a rule albumin is administered to humans, for example as a plasma expander, then in accordance with the invention human serum albumin (HSA) is advantageously used. Although the method of the invention can be used to remove many stabilizers or other ligands, it is particularly suited to removing the stabilizer molecules N-acetyl tryptophan and/or octanoic acid or their anions. Advantageously, the method can be used for ligands with a $K_a$ value (association constant) of more than $10^4$.

In a preferred implementation of the method of the invention, the starting albumin solution and the adsorption material are brought into contact in said step a) by feeding the starting albumin solution through a column containing the adsorption material (chromatographic column).

In an alternative implementation of the method of the invention, the starting albumin solution and the adsorption material are brought into contact in said step a) by feeding the starting albumin solution through a bed formed by the adsorption material. A particularly apt example is a gently moving fluidized bed which is moved using a slowly moving stirrer or vibrator or a counter-current. This prevents the channels or paths in a closely packed bed of adsorption material from being occupied by very small particles which inhibit or block the throughput of albumin solution.

As already mentioned, separation of the albumin solution from the adsorption material in said step b) is advantageously carried out by filtering the albumin solution through a particle filter, wherein the particle filter is selected so that the albumin molecules can pass through and the solid adsorption material is retained.

In a further preferred implementation of the method of the invention, the adsorption material particles are bound to or in a matrix. Suitable matrix materials are support textiles (for example polymer fiber textiles) or open-pored polymer foam structures (for example open-celled polyurethane foams). In a further alternative implementation, the particles of adsorption material are also simply formed into a solid bed reactor by mixing in highly porous particles as "spacers", which provides sufficient spacing of the adsorption material particles and suitable channel sizes. When fixing in highly porous open-celled polymer foams, it is also possible simultaneously or subsequently to produce channels, for example by boring. An advantageous packing with this implementation is a "loose" packing using the textile or support polymer, which provides a low perfusion back-pressure to the relatively highly viscous albumin solutions. Further, the specifications for the filter for retaining the micro-particles are much lower than in the implementations described above.

In a further preferred implementation of the method of the invention, steps a) and b) are repeated several times, preferably 2 to 6 times, wherein in each case the treated albumin solution obtained in step b) is fed back to step a). To improve the depletion rate, in step a) regenerated and/or fresh adsorption material is advantageously used for the removal of stabilizer molecules. This can be carried out by exchanging the adsorption material in the apparatus provided, but particularly preferably, several adsorption devices with adsorption material are arranged in series, through which the albumin solution is fed in succession.

In a further preferred implementation of the method of the invention, the amount of adsorption material compared with the albumin concentration in the starting albumin solution and/or the contact time between the starting albumin solution and the adsorption material in step a) is selected so that the albumin binding capacity (ABiC) of the albumin solution produced, measured in accordance with Klammt et al, is at least 60%, preferably at least 70%, particularly preferably at least 80% and more particularly preferably at least 90%. The amount of adsorption material required here and the contact time will depend on the starting albumin used and the apparatus used and can be determined by the skilled person using his general knowledge and skill.

In a further preferred implementation of the method of the invention, the amount of adsorption material used compared with the albumin concentration in the starting albumin solution and/or the contact time between the starting albumin solution and the adsorption material in step a) is selected so that the concentrations of bound and unbound stabilizer molecules, in particular N-acetyl tryptophan and/or octanoic acid or their anions, in the starting albumin solution is reduced to less than 70%, preferably less than 50%, particularly preferably less than 30% and more particularly preferably less than 10% of its starting concentration. The amount of adsorption material and the contact time will depend on the starting albumin used and the apparatus selected and can be determined by the skilled person using his general knowledge and skill.

In a further preferred implementation of the method of the invention, the amount of adsorption material used compared with the albumin concentration in the starting albumin solution and/or the contact time between the starting albumin solution and the adsorption material in step a) is selected so that the concentrations of bound and unbound stabilizer molecules, in particular N-acetyl tryptophan and/or octanoic acid or their anions, in the starting albumin solution is reduced to less than 3.5 mol/mol albumin, preferably less than 2.5 mol/mol albumin, particularly preferably less than 1.5 mol/mol albumin and more particularly preferably less than 0.5 mol/mol albumin of its starting concentration.

Particularly preferably, the adsorption material for carrying out the method of the invention is a particulate material which is packed in a column or a bed or a support matrix so that fluid-carrying channels are formed between the particles of adsorption material, wherein the mean diameter of the channels, taken over the total length of the channels formed between the particles of all of the adsorption material employed, is more than 100 nm and less than 1000 μm, preferably less than 500 μm, more preferably less than 300 μm and particularly preferably less than 200 μm, still more preferably less than 100 μm.

The smaller the channel diameter, the greater the possibility of or frequency at which the albumin molecules will come into contact with the walls of the channels formed by the adsorption material and the higher the depletion rate in the method of the invention. However, the dimensions of the channels must not be too small as the flow rate of the albumin would be slowed down too much. Thus, it has proved to be particularly advantageous if the mean diameter of the channels, taken over the total length of the channels formed by the particles of all of the adsorption material used, is more than 100 nm and less than 60 μm, particularly preferably less than 10 μm.

In a particularly preferred implementation of the method of the invention, the minimum contact time between the starting albumin solution and the adsorption material in step a) is selected so that:

$$dm[\mu m]/10\ [\mu m/min] \leq \text{contact time}[\min] \leq dm[\mu m]/0.1\ [\mu m/min],$$

wherein "dm" means the mean channel diameter, taken over the total length of the channels formed between the particles of all of the adsorption material used.

More efficient depletion occurs if the minimum contact time between the starting albumin solution and the adsorption material in step a) is selected so that:

$$dm[\mu m]/4\ [\mu m/min] \leq \text{contact time}[min] \leq dm[\mu m]/0.3\ [\mu m/min],$$

wherein "dm" means the mean channel diameter, taken over the total length of the channels formed between the particles of all of the adsorption material.

In a particularly preferred implementation of the method of the invention, the adsorption material is activated charcoal. The activated charcoal is advantageously used as a material which can form a suspension or as a powder, for example packed in a column or as a bed of adsorption material. It is important that the activated charcoal particles in the powder can form channels between the particles which on the one hand are sufficiently large to allow the albumin solution to flow through the adsorption material with a sufficient flow rate, and on the other hand are sufficiently narrow that the albumin molecules in the albumin solution can come into direct surface contact with the activated charcoal particles at a high frequency during flow through. Particularly preferably, the activated charcoal powder is such that the channels formed between the particles have the cited advantageous channel diameters. The mean diameter of the channels between the activated charcoal particles should thus, taken over the total length of the channels formed between the activated charcoal particles, be more than 100 nm and less than 1000 µm, preferably less than 500 µm, particularly preferably less than 300 µm, more preferably less than 200 µm and still more preferably less than 100 µm.

Alternatively, the activated charcoal can also be embedded as the adsorption material in a solid porous matrix, for example a polymer matrix formed from cellulose, resin or other polymer fibres or open-pored foams. When embedding the activated charcoal in a matrix, care should be taken that the matrix allows the albumin solution to flow in and that the matrix carries the activated charcoal particles in such a manner that they can come into contact with the albumin solution. Further, the porosity of the matrix material should be such that the pores can form channels with the channel diameters cited above to allow the albumin solution to flow through.

Advantageously, a support matrix with hydrophilic properties is used, which allows the adsorption material to be wetted. Such a support matrix can, for example, include cellulose or other natural or synthetically produced hydrophilic polymers.

Activated charcoal itself is a porous material which within its particle has macropores (>25 nm), mesopores (1-25 nm) and micropores (<1 nm), so that the activated charcoal has a very large internal surface area. The size of these pores is normally given for activated charcoal by the molasses number (macropores), the methylene blue adsorption (mesopores) and the iodine number (micropores). The internal surface area is determined using BET and given in $m^2/g$ activated charcoal. Activated charcoal is generally known as an adsorption medium which takes molecules into its pores and retains them therein or immobilizes substances by surface bonds. Because of the high porosity and internal surface area, activated charcoal has a very high adsorption capacity compared with its weight or external volume. This is dependent on the molecules being able to diffuse into these pores.

The state of the art regarding the preparation of commercial albumin solutions shows that only the use of activated charcoal alone is not sufficient to remove stabilizers which are very strongly bound to the albumin molecule in a stabilized albumin solution from the albumin molecule, in particular not at an acceptable rate. This is also confirmed by methods used until now for removing stabilizers from albumin solutions in which activated charcoal as an adsorption medium is added to a slurry, however without success at pHs of more than 3. Only following strong acidification and the accompanying structural alteration or denaturing of the albumin have known methods been successful in removing the stabilizer molecules from the albumin and successfully binding them to the activated charcoal.

The inventors have now discovered that a particular arrangement of particles of the adsorption material, in particular activated charcoal, namely advantageous dimensions of the channels between the particles leads to easier and faster release of stabilizer molecules which are strongly bound to the albumin molecules than before, under milder conditions such as a pH of >3. The channels have a mean diameter of more than 100 nm so that the albumin molecules can gain proper ingress. Thus, they must be substantially larger than the meso or micropores normally occurs in activated charcoal adsorption. The mean diameter of the channels should be no larger than 1000 µm. It has been shown that the rate of stabilizer removal from the albumin molecules is higher when the mean channel diameter is smaller, as long as it is more than 100 nm. Advantageously, the particles of adsorption material are arranged so that the channels have at least one inlet and one outlet so that albumin molecules which enter are not trapped therein but can then leave the channels.

Moreover, it was discovered that the rate of stabilizer removal when using activated charcoal as an adsorption material can be further improved if the activated charcoal, which can be obtained and produced in a variety of porosities and internal surface areas for use as an adsorption material, is selected so that it has a molasses number (IUPAC) of 100 to 400, preferably 200 to 300. More advantageously, it has a methylene blue adsorption (IUPAC) of 1 to 100 g/100 g of activated charcoal, preferably 10 to 30 g/100 g of activated charcoal, an iodine number (IUPAC) of 500 to 3000, preferably 800 to 1500, and/or a total internal surface area (BET) (IUPAC) of 100 to 5000 $m^2/g$ of activated charcoal, preferably 800 to 1400 $m^2/g$ activated charcoal.

The invention also concerns adsorption materials with the features defined above and its use in carrying out the method of the invention. Further, the invention also concerns the use of an aqueous albumin solution, produced using the method of the invention, for the production of a means for treating hypoalbuminaemia, a volume replacement medium or plasma expander and/or a means for improving the circulation, kidney and/or brain function of a patient. The medium is directed towards the stronger immobilization of physiological substances with an affinity to albumin.

The invention also concerns the use of an aqueous albumin solution produced using the method of the invention for the production of a means for purifying blood, as a plasma replacement means or as a dialysate for albumin dialysis. In particular for the latter application, an albumin solution produced in accordance with the invention is substantially cheaper than comparable solutions of ligand-free albumin, such as recombinant human serum albumin.

The method of the invention or an albumin solution produced in accordance with the method which is depleted in stabilizers is of great application in medicine. Patients with severe liver disease, hypotonus and hyperdynamic circulation problems have a limited albumin binding capacity (ABiC), which cannot be improved by currently available standard albumin preparations. Although in this connection it has not yet been borne out experimentally, in theory this limited binding capacity is a consequence of the endogenous accumulation of albumin-seeking toxins which can no longer be physiologically sufficiently broken down by the damaged liver. Attempts to build up this limited albumin binding capacity using commercial preparations of human serum albumin failed by overloading the preparations with stabilizers, as necessitated by the production method. However, these stabilizers are vital for the pasteurization of albumin solutions as regards virus protection and safe storage to prevent spontaneous polymerization. Removing these stabilizers has until now required extreme acidification and/or was associated with a large loss of albumin. The invention provides a method for production near to the point of use of an albumin solution with improved albumin binding capacity without active prior acidification.

The albumin solution produced in accordance with the invention can, inter alia, be used as a volume replacement means with a stabilizer-free albumin with a high binding capacity for vasoactive substances and toxins with an affinity for the diazepam binding sites of the albumins (Sudlow binding site ii). The method of the invention is cheap and economic as regards apparatus, so that it can readily be carried out, for example at the bedside shortly before infusion of the solution into a patient.

Because of the improved binding capacity of the albumin made in accordance with the invention, the albumin solution not only acts as a volume replacement, as previously assumed by a raised colloid osmotic i.e. water binding effect in the vessels, but also by actively immobilizing vasodilatory and other toxic substances. This results in a reduction in vasodilation and thus a synergistic effect of the volume replacement on the degree of filling of the vascular bed. Lastly, the considerable influence on mean arterial pressure and thus perfusion of the vessel system is shown by the diastolic blood pressure.

Further, the albumin solution produced in accordance with the invention can advantageously be used to improve the binding of ligands in albumin dialysis.

The method of the invention has the advantage that stabilizer depletion in an albumin solution can be carried out at a high rate, i.e. in a relatively short period. Thus, a commercial albumin solution can be treated within 10 to 30 minutes and the albumin binding capacity can be substantially raised. The method is thus suitable, inter alia, for bedside preparation of commercially stabilized albumin solutions although the invention is not limited thereto. Depletion in the pharmacies of clinics or other establishments or enterprises is also possible.

In accordance with the method of the invention, commercial albumin solutions stabilized with octanoic acid (octatoate) and/or N-acetyl tryptophan (N-acetyl tryptophanate) can be reduced to respective concentrations of these stabilizers of less than 5 mol/mol albumin, preferably less than 1 mol/mol albumin, particularly preferably less than 0.2 mol/mol albumin.

The invention will now be described in more detail using some examples.

Example 1

Adsorption Material Powder in Packed Column

In an experiment to compare the efficiency as regards the depletion of stabilizer molecules from stabilized albumin solutions, various adsorption material preparations were produced and tested.

For two preparations of adsorption material of the invention, a defined activated charcoal Norit GAC 830 (Norit) was processed by grinding in an industrial grinder to various particle sizes. The particle sizes of the ground products was then measured microscopically and using a commercial particle analyzer. For the first batch of the invention (A1), Norit GAC 830 was ground to a particle size of 1 mm (D50) and for the second batch (A2), Norit GAC 830 was ground to a particle size of 0.1 mm (D50). D50 corresponds to the $50^{th}$ percentile (see below). For comparison (V), a Norit ROX extruded charcoal (Norit) was used.

100 g of the activated charcoal materials were placed in a column with a diameter of 6 cm and a height of 10 cm provided with a sieve base and watered. 20 g of commercial albumin in 330 ml of salt solution (ZLB Behring, pH 7.2) recirculated at a rate of 170 ml/min was passed through the adsorption material in each column. At time zero and after 20, 30, 60 and 120 min, the concentrations of octanoic acid, N-acetyl tryptophan and albumin as well as the albumin binding capacity (Klammt et al, 2001) were determined. For the control, the values were also determined at times 240, 1440 and 2880 minutes. The results are shown in Table 1.

The Norit ROX extruded charcoal material formed very broad spaces or channels between the particles because of the extruded shape of the material when filled into a column, with a diameter which was sometimes over 1 mm, which is advantageous for the perfusion pressure, in particular at high rates of 100 to 250 ml/min. A comparison with batches A1 and A2 of the invention with ground activated charcoal showed, however, that this adsorption material with rather large channels is practically unsuitable for increasing the albumin binding capacity in a short period.

For powdered ground activated charcoal materials of batches A1 and A2 in the columns, the channel diameter was given by the following formula (I) to a good approximation:

$$R_K = [R_P^2 + (R_P * 0.57735)^2]^{0.5} - R_P \qquad (I)$$

where $R_K$ is the mean channel radius between the particles and $R_P$ is the mean radius of the particle itself.

For the ground particles of batch A1 with a mean diameter of 1 mm, i.e. a radius $R_P$ of 500 μm, the mean channel radius $R_K$ was 77 μm, i.e. a mean channel width (also mean diameter) of about 150 μm. For the ground particles of batch A2, with a mean diameter of 0.1 mm, i.e. a radius $R_P$ of 50 μm, the mean channel radius $R_K$ was 7.7 μm, i.e. a mean channel width (also mean diameter) of about 15 μm.

The results of this calculation of the channel widths based on the above formula was also confirmed by fixing samples of the column materials in resin and microscopic examination.

TABLE 1

| Contact time | Batch | Mean channel width [μm] | Octanoate/ albumin [mol/mol] | NAC/ albumin [mol/mol] | ABiC [%] |
|---|---|---|---|---|---|
| 0 | V | 1000 | 5.2 | 5.2 | 45 |
|  | A1 | 150 | 5.2 | 5.2 | 45 |
|  | A2 | 15 | 5.2 | 5.2 | 45 |
| 20 | V | 1000 | 1.05 | <0.2 | 48 |
|  | A1 | 150 | 0.9 | <0.2 | 63 |
|  | A2 | 15 | 0.4 | <0.2 | 82 |
| 30 | V | 1000 | 0.96 | <0.2 | 51 |
|  | A1 | 150 | 0.9 | <0.2 | 65 |
|  | A2 | 15 | 0.3 | <0.2 | 95 |
| 60 | V | 1000 | 0.69 | <0.2 | 56 |
|  | A1 | 150 | 0.4 | <0.2 | 80 |
|  | A2 | 15 | 0.2 | <0.2 | 100 |

TABLE 1-continued

| Contact time | Batch | Mean channel width [μm] | Octanoate/ albumin [mol/mol] | NAC/ albumin [mol/mol] | ABiC [%] |
|---|---|---|---|---|---|
| 120 | V | 1000 | 0.36 | <0.2 | 75 |
|  | A1 | 150 | 0.2 | <0.2 | 95 |
|  | A2 | 15 | 0.1 | <0.2 | 110 |
| 240 | V | 1000 | 0.23 | <0.2 | 81 |
| 1440 | V | 1000 | 0.07 | <0.2 | 96 |
| 2880 | V | 1000 | 0.05 | <0.2 | 103 |

The results with Norit ROX confirm the above description, that under physiological conditions, in particular at a neutral pH, a substantial depletion in stabilizers under the experimental conditions used until now, i.e. the use of activated charcoal powders or suspensions with large channel widths, is not possible in 60 minutes, at least not in an amount which substantially raises the albumin binding capacity.

Surprisingly, extending the contact time according to the data given in this application can produce a depletion in octanoic acid even with this activated charcoal, which results in an increase in the albumin binding capacity.

According to the guidelines for estimating the minimum required contact time as a function of the channel width, for a mean width (dm) of 1000 μm, the contact time should be extended to over 250 min. The experiments show that at 240 min the ABiC is only just over 80%, an acceptable value of over 90% only being measured after one day (1440 min).

On investigating the surface structure of the test activated charcoal, it was shown that only a disappearingly small fraction of the albumin molecule could actually come into direct contact with the activated charcoal surface as on the one hand only the macropores could allow the albumin molecule a certain ingress, while the vast majority of the mesopores are too small to allow albumin to pass. The macropores, however, constitute a disappearingly small fraction of the pores and branch very quickly immediately beneath the external surface into mesopores which can no longer be transited by the albumin molecule. Where macropores allow the ingress of the albumin molecule, for the most part the albumin molecules are trapped in the pores, which particularly with macroporous activated charcoals can result in a high loss of albumin.

The test batches A1 and A2 show that this problem can be solved by creating narrower mean channel widths, for example by using particles with a smaller mean diameter in a powder. The results further confirm that the arrangement of the adsorption material plays an essential role in the effectiveness of removal of stabilizers, which cannot automatically be achieved by the choice of adsorber alone.

In the method of the invention, on the other hand, an adsorption material is used which has channels which are dimensioned to match the albumin molecule. The whole length of these channels can be transited by the albumin molecule and are dimensioned so that the albumin molecules come into very frequent and close contact with the surface of the adsorption material. The channels are characterized by their mean internal width or their mean diameter.

Example 2

Suspensions of Activated Charcoal Particles in Fluidized Bed Reactors

In order to demonstrate that it is not enlarging the external surface of the activated charcoal by the grinding method but the adjusting the channels between the particles by the material to optimized mean channel diameters which is responsible for the success of the invention, in a further experiment adsorption materials with the same external surface area were examined with only the channel width being varied. The appropriate experimental vehicle in this case was the fluidized bed, in which fine particulate adsorption material is held in suspension by stirring, vibrating or convective or turbulent streaming.

In the fluidized bed, the spaces formed between the evenly distributed particles in the suspension form channels for the flow of the albumin. The channel diameter in the fluidized bed can be given to a good approximation using the following formula (II):

$$D_K = [V_{WB}^{0.33} - (n^{0.33} * D_P)] / n^{0.33} \quad (II)$$

wherein $D_K$ is the mean channel diameter between the particles, $D_P$ the mean diameter of the particle itself, n is the number of particles and $V_{WB}$ is the volume of the fluidized bed.

The volume of the fluidized bed for a desired mean channel diameter is given by solving formula (II) for volume by using the following formula (IIa):

$$V_{WB} = [(n^{0.33} * D_P) + (n^{0.33} * D_K)]^3 \quad (Ia)$$

To determine the channel diameter, then, only the volume of the fluidized bed, the particle number and the particle size have to be batch so that the desired channel diameter can be obtained. The mean particle diameter $D_P$ and also the bulk density required to estimate the number of particles in the mass are either given by the manufacturer or can be determined using simple standard procedures.

The number of particles n in a dry powder can for practical purposes be determined by the bulk density (packed) and the particle size using the following formula (III):

$$n = [V_{TS}^{0.33} / (0.86 * D_P)]^3 \quad (III)$$

wherein n is the number of particles in a dry powder volume, $V_{TS}$ is the volume of the packed dry powder and $D_P$ is the mean particle diameter. If the dry powder density is given for a particular adsorption material, the volume $V_{TS}$ can also be calculated by dividing the weight by the dry powder density.

Since in practice the particles are not always ideally spherical and also frequently not always the same size, for particles with a broad size distribution it must in practice be assumed that the distribution of spaces in a suspension in the adsorber fluidized bed is dependent on the size distribution of the adsorber particles. As a rule, particularly with powdered adsorbers (for example with Norit C Extra USP), the characterizing numbers of the particle distribution are given, i.e. the percentiles in the size distribution e.g. D10 and D90. Using the D10 and D90 values, a size distribution range can be described which encompasses about 80% of the particles. Thus, the volume in which a defined weight or dry powder volume can be distributed in a fluidized bed can be estimated in a practical manner, to produce the desired channel diameter to a good approximation.

In this case, the calculations of the fluidized bed volume can be carried out using the D10 value instead of $D_P$ and then the D90 value instead of $D_P$, in order to determine the upper and lower limits of the fluidized bed volume in which the separation in accordance with the invention between the adsorber particles (channel width) is optimized in accordance with the invention. The calculation on the basis of the D90 value will result in a maximum variation for which it is possible to de-ligand with effective raising of the albumin binding capacity (ABiC) with certainty.

The influence of channel width was determined as follows. Different volumes of an activated charcoal-albumin mixture of 1 g of activated charcoal/1 g of albumin (activated charcoal: Norit C Extra USP from Norit Nederland BV, Netherlands; commercial albumin, stabilized with 5.2 mmole of octanoate and 5.2 mmol of N-acetyl tryptophanate per mmol albumin) were added to a fluidized bed in a NaCl solution and stirred for 30 minutes at room temperature. After the treatment period, the activated charcoal particles were separated from the albumin solution by centrifuging. Next, the albumin, octanoate and N-acetyl tryptophanate concentrations and the ABiC were measured and observed in relation to the channel widths obtained. The results are shown in Table 2.

TABLE 2

| Test | Weight [g] | n50 | n10 | n90 | Fluidized bed volume [ml] | Dk50 [μm] | Dk10 [μm] | Dk90 [μm] | Oct/Alb | NAC/Alb | ABiC [%] |
|---|---|---|---|---|---|---|---|---|---|---|---|
| 1 | 0.5 | $3 \times 10^8$ | $2.94 \times 10^{10}$ | $6.7 \times 10^6$ | 3.25 | 5.2 | 1.2 | 17.2 | <0.2 | <0.2 | 110 |
| 2 | 0.5 | $1.5 \times 10^8$ | $1.48 \times 10^{10}$ | $3.36 \times 10^6$ | 7.5 | 12.3 | 2.8 | 42.4 | 0.20 | <0.2 | 83.2 |
| 3 | 0.5 | $1.5 \times 10^8$ | $1.48 \times 10^{10}$ | $3.36 \times 10^6$ | 10 | 15.9 | 3.6 | 54.8 | 0.22 | <0.2 | 79.9 |
| 4 | 0.5 | $1.5 \times 10^8$ | $1.48 \times 10^{10}$ | $3.36 \times 10^6$ | 12.5 | 18.8 | 4.2 | 65.3 | 0.27 | <0.2 | 70.3 |
| 5 | 0.5 | $1.5 \times 10^8$ | $1.48 \times 10^{10}$ | $3.36 \times 10^6$ | 22.5 | 27.8 | 6.2 | 96.8 | 0.43 | <0.2 | 67.5 |
| 6 | 0.5 | $1.5 \times 10^8$ | $1.48 \times 10^{10}$ | $3.36 \times 10^6$ | 32.5 | 34.3 | 7.6 | 119.8 | 0.58 | <0.2 | 63.3 | n50, n10, n90 = particle size, calculated using formula (III) using the d50, D10 or D90 percentiles as the mean particle diameter.
Dk50, Dk10, Dk90 = mean channel diameter, calculated using formula (II) using the d50, D10 or D90 percentiles as the mean particle diameter.
Oct/Alb = molar ratio of octanoic acid to albumin.
NAC/Alb = molar ratio of N-acetyl tryptophan to albumin.

The results clearly show that an increase in the mean channel diameter (DK50) in the fluidized bed, which stands in a direct relationship with the increase in the fluidized bed volume in the above formula (II) for a constant particle type and number, independently of the exterior surface area of the adsorption material leads to a decrease in the effectivity of the depletion of octanoate and N-acetyl tryptophan and the resulting albumin binding capacity.

Similarly, the table shows that using the rule for a preferred implementation of the invention:

$$d_m[\mu m]/4\ [\mu m/min] \leq \text{contact time}[min] \leq d_m[\mu m]/0.3\ [\mu m/min],$$

an optimal depletion is then attained within 30 minutes when the channel width is selected so that the upper limit for the minimum required contact time is less than 30 minutes (test 1). In this case the upper limit for the minimum necessary contact time, relative to the mean channel diameter of 5.2 μm, is 17.3 min, whereas a maximum depletion of NAC and octanoic acid occurs and the ABiC reaches a value of 110%. In tests 2 to 6, this upper value for the minimum contact time was not exceeded. Thus, very good depletions and improved ABiCs were observed, but the optimum value of test 1 was not achieved.

Examples 1 and 2 show that the contact time required between the albumin solution and the adsorption material for effective stabilizer depletion is strongly dependent on the mean diameter of the channels in the adsorption material. By matching the mean diameter of the channels in the adsorption material, the required contact times can be influenced and also, for example, the throughput rate of the albumin solution in a column packed with adsorption material can be influenced.

Example 3

Fixing Adsorbers in Textiles, Open-Celled Foams or Mixed Powders

In the embodiment described below, the inventive distances between the adsorber particles, i.e. the channel widths, were "fixed" in a network which could be perused.

The particles of adsorption materials, for example activated charcoal, can thus be made into the form of a solid bed reactor using support textiles (for example polymer fibers), open-pored polymer foam structures (for example open-celled polyurethane foam) or simply by mixing highly porous particles as the "spacers", which provides a sufficient spacing for the adsorption material particles from each other and thus provides the channel width batch by the invention. On fixing in highly porous, open-celled polymer foams, it is also possible at the same time or subsequently, to make channels, for example by drilling procedures. These channel widths also satisfy the rule which defines the relationship between the channel width and the minimum necessary contact time, in accordance with the invention.

Advantageously, in this embodiment a "loose" packing is obtained using textile or support polymer which causes relatively little perfusion back pressure on the highly viscous albumin solutions. In addition, the filtration requirements to retain micro particles does not to be as great as in the embodiments described above.

Again, when fixing adsorbers in textiles, open-celled foams or mixed powders, the mean channel diameter is given by formula (IV) to a close approximation:

$$D_K = [V^{0.33} - (n^{0.33} * D_P)]/n^{0.33} \quad (IV)$$

wherein $D_o$ is the mean channel diameter between the particles, $D_P$ is the mean diameter of the particle itself, n is the number of particles and V is the volume of the textile, mixed powder or foam in the final state. A desired channel diameter can be determined, for a known particle number and known particle diameter, by calculating the appropriate volume using formula IV:

$$V = [(n^{0.33} * D_P) + (n^{0.33} * D_K)]^3 \quad (IVa)$$

The bases of calculation for the advantageous combination of adsorber weight and end volume correspond to the bases of calculation of Example 2.

In an experiment, 2 g of activated charcoal (Norit C Extra USP from NORIT Nederland BV, Netherlands) with a mean particle size of 23 μm (D50) (D10=5 μm, D90=82 μm) was mixed in an aqueous suspension/solution formed from a fibrous polymer (in this case cellulose) and a polymer with a tendency to cross-link (for example resins, polyurethane, polyacrylmethacrylates, etc), wherein the channel width was set to 3.6 μm, to achieve appropriate deligandisation in less than 12 minutes of contact time. According to the formula of the invention:

$$dm[\mu m]/4\ [\mu m/min] \leq \text{contact time}[min] \leq dm[\mu m]/0.3\ [\mu m/min],$$

the upper limit of the minimum contact time is 12 minutes. Using formula (IVa), for a weight of 2 g a volume of 12.5 ml, was given which corresponded to the final total volume of the mixture. The mixture was added to a close mesh net with a surface area of about 25 cm² with pores which were small enough not to allow adsorber particles and cross-linked support polymers to pass (for example 5 μm mesh). The mixture was distributed on the net so that after draining though a pressure gradient (1 atm) a dry thickness of 5 mm was achieved. The adsorption material produced had an end volume of 12.5 ml in total. The mean channel diameter $D_k$, calculated using formula (IV) above and using a particle size d50 of 23 μm, was 3.6 μm.

10 ml of a 20% commercial stabilized albumin solution was fed through the adsorption material at a rate of 1 ml/min perpendicular to the surface of the net in a commercial filtration apparatus in the same flow direction as that of the pressure gradient on drying. The albumin binding capacity of the treated albumin solution had increased from 45% to over 100% by removal of stabilizers within 10 minutes using this process. The ratio of octanoate and N-acetyl tryptophanoate to albumin was less than 0.2 mmol/mmol.

Example 4

Clinical Application

In clinical trials, the effects of the albumin solutions of the invention with an increased albumin binding capacity were investigated. A prospective randomized population of 30 patients with liver failure from chronic ethyltoxic cirrhosis and superimposed hepatitis C2 with a bilirubin level of over 20 mg/dl and limited protein synthesis (raised INR) with hypotonic and hyperdynamic circulation were divided into 2 groups. One group was treated with the albumin solution with an increased albumin binding capacity of the invention and the control group was not. Circulation parameters and final organ functions of the kidney and brain were regularly monitored during the duration of the test and the observation time of 2 weeks.

The results are shown in the accompanying drawings.

Figure 1:
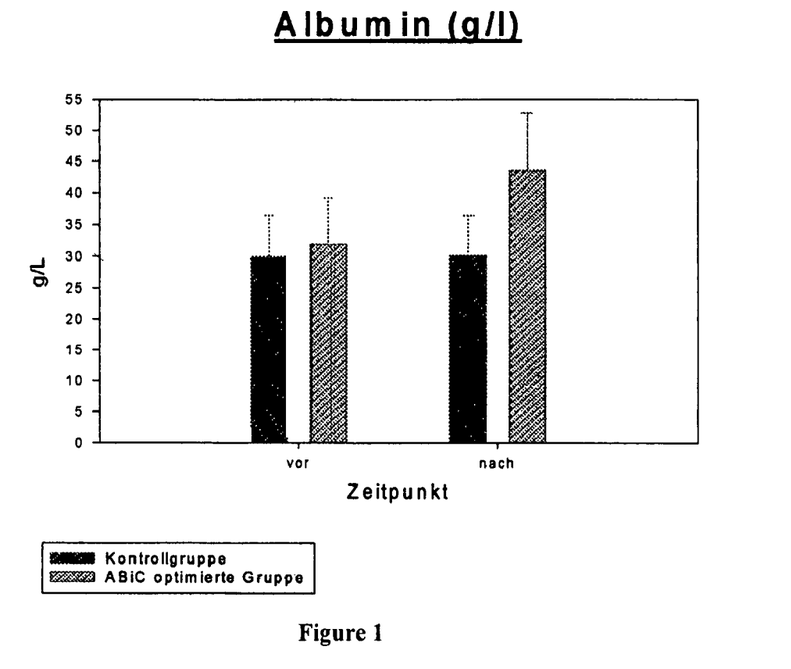
FIG. 1 shows the albumin concentration in the blood of the two test groups before therapy and after two weeks.
Figure 2:
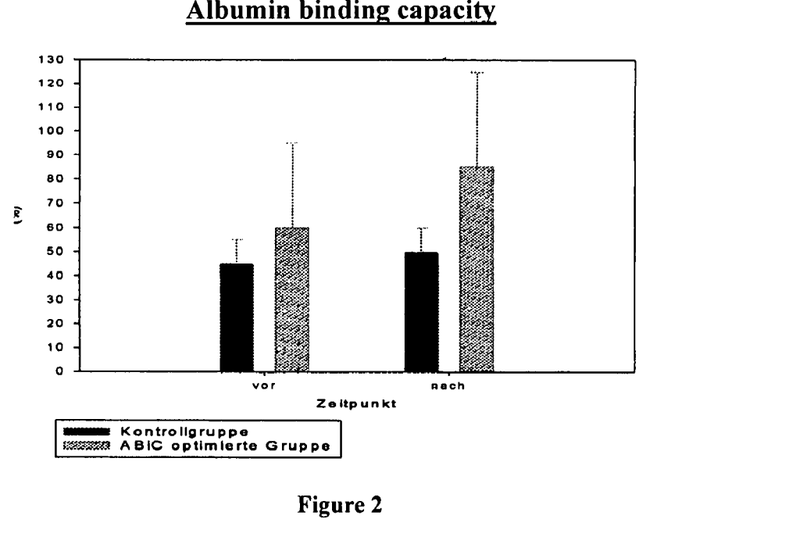
FIG. 2 shows the albumin binding capacity of the albumin in blood from both test groups before therapy and after two weeks.
Figure 3:
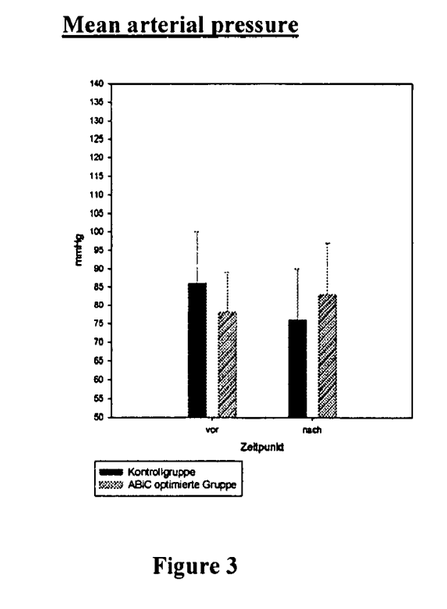
FIG. 3 shows the change in the mean arterial pressure of both test groups before therapy and after two weeks.
Figure 4:
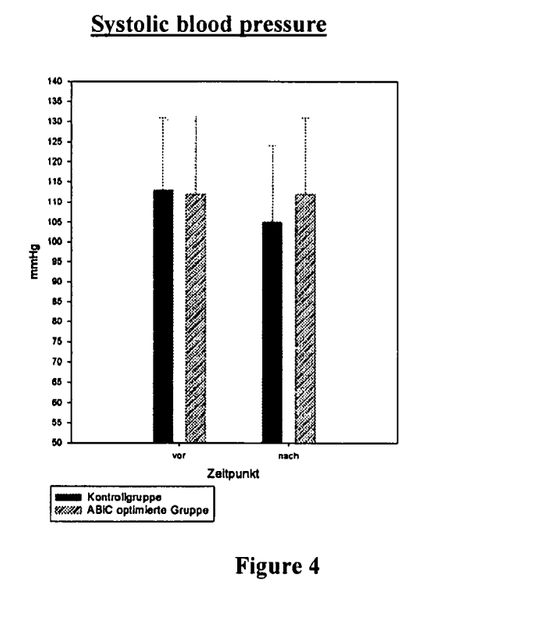
FIGS. 4, 5, 6 show the systolic blood pressure, the diastolic blood pressure and the heart rates of both test groups before therapy and after two weeks.
Figure 5:
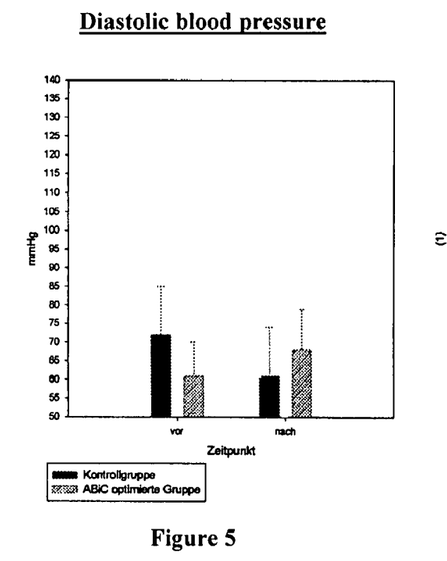
Figure 6:
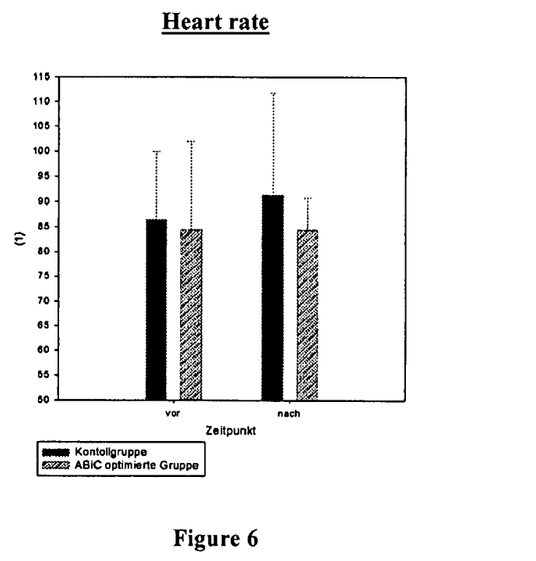
Figure 7:
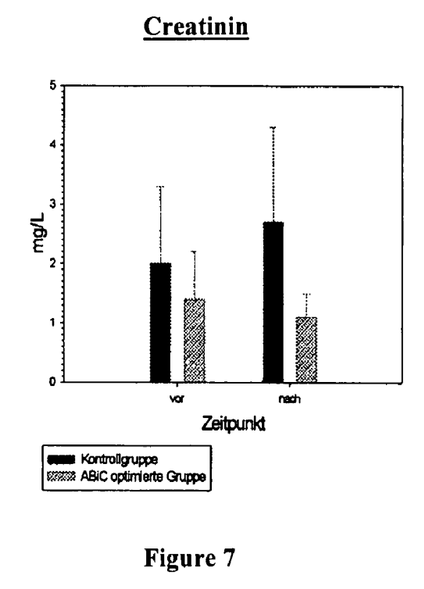
FIG. 7 shows the effect on kidney function, measured for creating, of both test groups before therapy and after two weeks.
Figure 8:
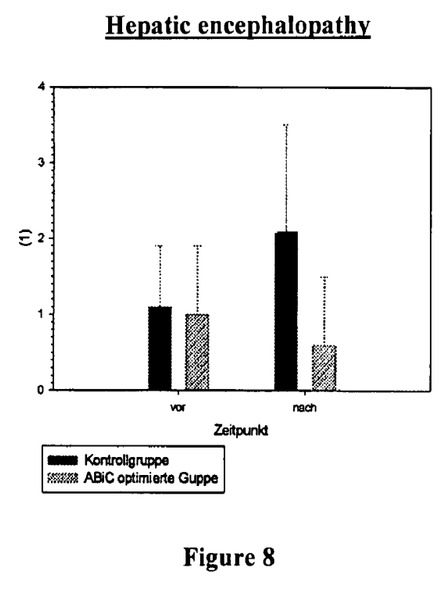
FIG. 8 shows the effect on hepatic encephalopathy, which is a result of toxins which limit blood to the brain and seek albumin and of changes in blood flow, of both test groups before therapy and after two weeks.

The results of the clinical tests show that an improvement in the albumin binding capacity (ABiC) is associated with an improvement in mean arterial pressure, which clearly is brought about by an increase in the diastolic blood pressure than by an increase in heart rate. This medically indicates a reduced vasodilation which in liver disease is often the effect of vasodilatory substances with an affinity for albumin. Immobilizing them with improved albumin binding thus improves the circulation, kidney and brain function. Finally, improved binding of directly neurotoxic substances, which substances also bind to albumin with an improved ABiC can also occur in addition to the improved blood pressure situation.

What is claimed is:

1. A method for producing an aqueous albumin solution from a starting albumin solution which contains stabilizer molecules which are capable of occupying binding sites of the albumin, by removing at least a portion of the stabilizer molecules from the starting albumin solution comprising the steps of:
   a) bringing the starting albumin solution into contact with a solid adsorption material having an affinity for at least a portion of the stabilizer molecules that is higher than the affinity of the albumin for the corresponding stabilizer molecules at a pH $\geq 5$; wherein the adsorption material is a particulate activated charcoal material packed in a column or a bed or a support matrix so that fluid-carrying channels are formed between the particles of adsorption material, wherein the mean diameter of the channels, relative to the total length of the channels formed between particles of all of the adsorption material employed, is more than 100 nm and less than 1000 μm; and
   b) separating the albumin from the adsorption material.

2. A method according to claim 1 wherein the method is carried out at a pH in the range of 5 to 9.

3. A method according to claim 1 wherein the method is carried out at a pH in the range of 6 to 8.

4. A method according to claim 1 wherein the method is carried out at a pH in the range of 6.9 to 7.5.

5. A method according to claim 1 wherein the albumin is human serum albumin (HSA).

6. A method according to claim 3 wherein the albumin is human serum albumin (HSA).

7. A method according to claim 1 wherein the stabilizer molecules to be removed include at least one of N-acetyl tryptophan, octanoic acid, anions of N-acetyl tryptophan and anions of octanoic acid.

8. A method according to claim 1 wherein the starting albumin solution and the adsorption material are brought into contact in step a) by feeding the starting albumin solution through a column containing the adsorption material or through a bed formed by the adsorption material.

9. A method according to claim 1 wherein separation of the albumin solution from the adsorption material in step b) is carried out by filtering the albumin solution through a particle filter, wherein the particle filter is selected so that the albumin molecules can pass through and the solid adsorption material is retained.

10. A method according to claim 1 wherein steps a) and b) are repeated such that treated albumin solution obtained in step b) is fed back to step a), and in step a) the adsorption material comprises regenerated adsorption material, fresh adsorption material or mixtures thereof.

11. A method according to claim 1 wherein a combination of the amount of adsorption material used compared with the albumin concentration in the starting albumin solution and the contact time between the starting albumin solution and the adsorption material in step a) is selected so that the albumin binding capacity (ABiC) of the albumin solution produced is at least 60%.

12. A method according to claim 1 wherein a combination of the amount of adsorption material used compared with the albumin concentration in the starting albumin solution and the contact time between the starting albumin solution and the adsorption material in step a) is selected so that the albumin binding capacity (ABiC) of the albumin solution produced is at least 80%.

13. A method according to claim 1 wherein a combination of the amount of adsorption material used compared with the albumin concentration in the starting albumin solution and the contact time between the starting albumin solution and the adsorption material in step a) is selected so that the albumin binding capacity (ABiC) of the albumin solution produced is at least 90%.

14. A method according to claim 1 wherein a combination of the amount of adsorption material used compared with the albumin concentration in the starting albumin solution and the contact time between the starting albumin solution and the adsorption material in step a) is selected so that the concentration of stabilizer molecules in the starting albumin solution is reduced to less than 50%.

15. A method according to claim 1 wherein a combination of the amount of adsorption material used compared with the albumin concentration in the starting albumin solution and the contact time between the starting albumin solution and the adsorption material in step a) is selected so that the concentration of stabilizer molecules in the starting albumin solution is reduced to less than 30%.

16. A method according to claim 1 wherein a combination of the amount of adsorption material used compared with the albumin concentration in the starting albumin solution and the contact time between the starting albumin solution and the adsorption material in step a) is selected so that the concentration of stabilizer molecules in the starting albumin solution is reduced to less than 10%.

17. A method according to claim 1 wherein the mean diameter of the channels, relative to a total length of the channels formed between the particles of all of the adsorption material employed is less than 300 μm.

18. A method according to claim 17 wherein the mean diameter of the channels is more than 100 nm and less than 60 μm.

19. A method according to claim 1 wherein minimum contact time between the starting albumin solution and the adsorption material in step a) is selected so that:

$$dm(\mu m)/10\ (\mu m/min) \leq \text{contact time(min)} \leq dm(\mu m)/0.1\ (\mu m/min),$$

wherein "dm" means the mean channel diameter, taken over the total length of the channels formed between the particles of all of the adsorption material.

20. A method according to claim 1 wherein minimum contact time between the starting albumin solution and the adsorption material in step a) is selected so that:

$$dm(\mu m)/4(\mu m/min) \leq \text{contact time(min)} \leq dm(\mu m)/0.3\ (\mu m/min),$$

wherein "dm" means the mean channel diameter, taken over the total length of the channels formed between the particles of all of the adsorption material.

21. A method according to claim 1 wherein the activated charcoal has a molasses number (IUPAC) of 100 to 400.

22. A method according to claim 1 wherein the activated charcoal has a methylene blue adsorption (IUPAC) of 10 to 100 g/100 g of activated charcoal.

23. A method according to claim 1 wherein the activated charcoal has an iodine number (IUPAC) of 500 to 3000.

24. A method according to claim 1 wherein the activated charcoal has a total internal surface area (BET) (IUPAC) of 800 to 5000 $m^2$/g of activated charcoal.

* * * * *